United States Patent [19]

Fäh

[11] 4,214,086
[45] Jul. 22, 1980

[54] PROCESS FOR PRODUCING HYDROXYDIARYL ETHERS

[75] Inventor: Hansjakob Fäh, Ettingen, Switzerland

[73] Assignee: Ciba-Geigy Corporation, Ardsley, N.Y.

[21] Appl. No.: 37,561

[22] Filed: May 9, 1979

Related U.S. Application Data

[63] Continuation of Ser. No. 848,671, Nov. 4, 1977, abandoned.

[51] Int. Cl.² .................. C07D 213/63; C07D 213/64
[52] U.S. Cl. ............................. 546/290; 260/465 F; 560/61; 562/471; 568/586; 568/637; 568/638; 568/333
[58] Field of Search ................ 260/613 R, 297 R; 546/290

[56] References Cited

FOREIGN PATENT DOCUMENTS 2658496  6/1978  Fed. Rep. of Germany ...... 260/613 R

OTHER PUBLICATIONS

Gitis et al., Zh. Ongan. Khim., vol. 1, pp. 906–908, (1965) English Version (translation from orginal, pp. 887–889 of Russian version).
Gitis et al., Zh. Organ. Khim., vol. 2, pp. 107–109, (English version 1966), translated from Russian version, pp. 112–114.
Butakus et al., Zh. Organ. Khim., vol. 5, pp. 521–522, (1968), (English version, translated from Russian version, pp. 533–534.

Primary Examiner—John D. Randolph
Attorney, Agent, or Firm—Karl F. Jorda

[57] ABSTRACT

A process for producing hydroxydiaryl ethers of the formula

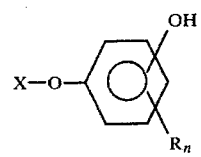

wherein R respesents an alkyl group having 1 to 4 carbon atoms or chlorine, n represents 0, 1, 2, 3 or 4, and X represents a phenyl group of the formula II

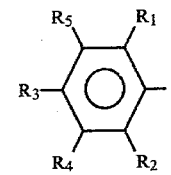

or a 2-pyridinyl group or a 4-pyridinyl group of the formulae

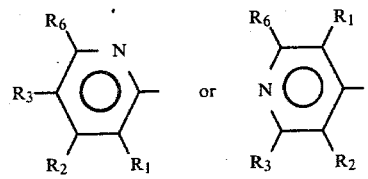

wherein $R_1$, $R_2$ and $R_3$ each represent hydrogen, an alkyl group having 1 to 4 carbon atoms, an alkyl group which has 1 to 4 carbon atoms and which is mono- or disubstituted by halogen, phenyl, halogen, carboxyl, alkoxycarbonyl having 1 to 4 carbon atoms in the alkyl group, trifluoromethyl, nitro, cyano or benzoyl, $R_4$ and $R_5$ each represent hydrogen, an alkyl group having 1 to 4 carbon atoms or phenyl, and $R_6$ has all the meanings given, with the exception of halogen, for $R_1$, $R_2$ and $R_3$ is disclosed.

According to this process hydroxydiaryl ethers of the above formula are obtained by reacting a diether of the formula

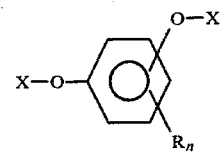

wherein R, n and X have the meanings given above, in a polar aprotic solvent, in the presence of 0.1 to 1 mole of alkali per mole of diether of the above formula, with a dihydroxybenzene of the formula

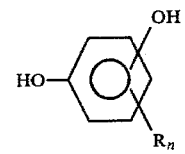

wherein R and n have the meanings given above.

The hydroxydiaryl ethers of the above formula can be used as intermediates for the production of α-(phenoxyphenoxy)-alkanecarboxylic acid derivatives and α-(pyridyloxy-phenoxy)-alkane carboxylic acid derivatives, which have a herbicidal and plant-growth-regulating action.

12 Claims, No Drawings

PROCESS FOR PRODUCING HYDROXYDIARYL ETHERS

This is a continuation of application Ser. No. 848,671 filed on Nov. 4, 1977, now abandoned.

The present invention relates to a process for producing hydroxydiaryl ethers of the formula I

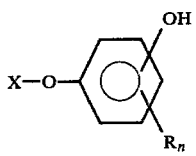
(I)

wherein R represents an alkyl group having 1 to 4 carbon atoms or chlorine, n represents 0, 1, 2, 3 or 4, and X represents a phenyl group of the formula II

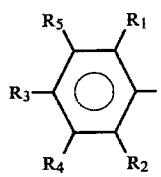
(II)

or a 2-pyridinyl group of the formula IIa or a 4-pyridinyl group of the formula IIb

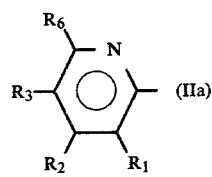 (IIa) 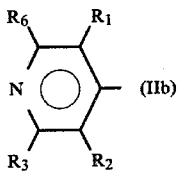 (IIb)

wherein $R_1$, $R_2$ and $R_3$ each represent hydrogen, an alkyl group having 1 to 4 carbon atoms, an alkyl group which has 1 to 4 carbon atoms and which is mono- or disubstituted by halogen, phenyl, halogen, carboxyl, alkoxycarbonyl having 1 to 4 carbon atoms in the alkyl group, trifluoromethyl, nitro, cyano or benzoyl, $R_4$ and $R_5$ each represent hydrogen, an alkyl group having 1 to 4 carbon atoms or phenyl, and $R_6$ has all the meanings given, with the exception of halogen, for $R_1$, $R_2$ and $R_3$.

The hydroxydiaryl ethers of the formula I are valuable intermediates that can be converted by reaction with lower α-halogenoalkanecarboxylic acid derivatives, e.g. α-halogenoalkanecarboxylic acid esters, in the presence of an acid-binding agent, into the corresponding α-(phenoxy-phenoxy)-alkanecarboxylic acid derivatives and α-(pyridyloxy-phenoxy)-alkanecarboxylic acid derivatives, which have a herbicidal and plant-growth-regulating action. Such α-(phenoxy-phenoxy)- and α-(pyridyloxy-phenoxy)-alkanecarboxylic acid derivatives are described, for example, in the Swiss patent applications Nos. 15033/75 of November 20, 1975, 15034/75 of Nov. 20, 1975, 8829/76 of July 9, 1976, 5951/77 of May 12th, 1977, 9321/76 of July 21, 1976, 9470/76 of July 23, 1976, 9471/76 of July 23, 1976 and 8023/77 of June 29, 1977; and in the corresponding U.S. patent applications Nos. 742311 of Nov. 16, 1976, 812087 of July 1, 1977, 814826 of July 12, 1977 and 816840 of July 18, 1977. α(Pyridyloxy-phenoxy)-alkanecarboxylic acid derivatives are also described in the German Offenlegungsschrift No. 2546251.

The product of hydroxydiaryl ethers of the formula I by reaction of a halogenobenzene containing an activated halogen atom, or of a 2- or 4-halogenopyridine, with a corresponding dihydroxybenzene in the presence of basic substances, particularly hydroxides and carbonates of alkali metals, in a polar aprotic solvent is known. The usefulness of this method of production is however impaired by the fact that there are formed, in addition to the desired hydroxydiaryl ethers of the formula I, varying amounts of diethers of the formula

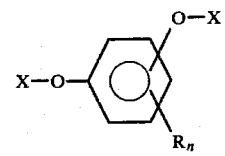

and in some cases these amounts are considerable. This necessitates an additional purifying operation in which the desired hydroxydiaryl ethers of the formula I have to be separated from the diethers of the above formula and from unreacted dihydroxybenzene.

In order to avoid the undesired formation of diethers it has already been suggested to react halogenobenzenes having activated halogen with monoethers of dihydroxybenzenes, and to subsequently split off the protective group (see U.S. Pat. Nos. 2,926,093 and 3,240,706).

It has also been already suggested that the formation of diethers occurring on reaction of halogenobenzenes with activated halogen and dihydroxybenzenes be avoided by using less than 1 mole, preferably less than 0.8 mole, of halogenobenzene per mole of dihydroxy compound, and using per mole of dihydroxy compound 1 mole of alkali (see German Offenlegungsschrift No. 2,157,781).

It is also known to produce hydroxydiphenyl ethers by reaction of halogenobenzenes and dihydroxybenzene in the presence of 2 moles of alkali per mole of dihydroxybenzene in a polar aprotic solvent (see German Offenlegungsschriften Nos. 2,433,066 and 1,911,799).

It is also already known to react 2-halogenopyridines with hydroquinone in the presence of 1 to 1.2 moles of alkali per mole of hydroquinone to give pyridyl-2-oxy-4-hydroxyphenyl ethers (see German Offenlegungsschrift No. 2,546,251).

It has now been found that hydroxydiaryl ethers of the formula I can be produced in a simple manner by reacting a diether of the formula III

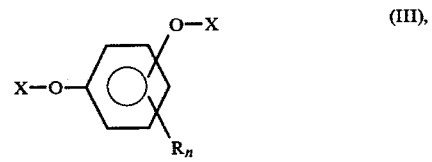
(III), wherein R, n and X have the meanings given under the formula I, in a polar aprotic solvent, in the presence of 0.1 to 1 mole of alkali per mole of diether of the formula III, with a dihydroxybenzene of the formula IV

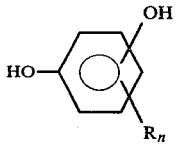

(IV)

wherein R and n have the meanings given under the formula I.

The diethers of the formula III and the dihydroxybenzenes of the formula IV are used essentially in equimolar amounts. In certain cases an excess of dihydroxybenzene can be of advantage. The molar ratio of diether of the formula III to dihydroxybenzene of the formula IV is preferably 1:1 to 1:1.1.

The process according to the invention is performed at elevated temperature, with reaction temperatures of between 40° and 200° C. having proved satisfactory. The process is preferably performed at a temperature of between 80° and 150° C.

Suitable polar aprotic solvents are, for example, dimethylsulphoxide, dimethylformamide, dimethylacetamide, diethylacetamide, hexamethylphosphoric acid triamide, tetramethylurea, sulpholane, N-methylpyrrolidone, acetonitrile and methyl ethyl ketone. A particularly suitable solvent is dimethylsulphoxide. It is advantageous in some cases to add to the aforementioned polar aprotic solvents, for the purpose of removing the water present in the reaction mixture, a further solvent which forms with water an azeotrope. Suitable additional solvents are for example toluene and xylene.

Suitable alkaline substances, in the presence of which the process according to the invention is performed, are hydroxides, carbonates and hydrogen carbonates of alkali metals. Preferred alkaline substances are sodium hydroxide and potassium hydroxide. The alkaline substance can be used according to the invention in an amount of 0.1 to 1 equivalent per mole of dihydroxybenzene of the formula IV. There is preferably used one equivalent of alkaline substance per mole of dihydroxybenzene of the formula IV.

The diethers of the formula III which are required as starting material can be obtained in a simple manner by reaction of a dialkali salt of a dihydroxybenzene of the formula IV with 2 moles of a halogenobenzene or halogenopyridine of the formula V X—Hal (V), wherein X has the meaning given under the formula I, and "Hal" denotes chlorine or bromine, in a polar aprotic solvent. Such a production process for diethers of the formula III is described for example in the German Offenlegungsschrift No. 1,932,298. Suitable dihydroxybenzenes of the formula IV are hydroquinones, resorcinols and brenzcatechins all optionally substituted according to the above definition of R and n. These starting materials can be obtained by methods known per se. There is used in each case the dihydroxybenzene of the formula IV already present in the diether of the formula III. Since however a dihydroxybenzene of the formula IV engages in the reaction merely with one of its two hydroxyl groups, it is necessary with use of substituted dihydroxybenzenes of the formula IV, for the formation of homogeneous reaction products, that the substituents present be so arranged with respect to the hydroxyl groups that on reaction of the one or other of the hydroxy groups there is always formed the same reaction product. The possible arrangement of the maximum of four substituents of the dihydroxybenzene of the formula IV usable according to the invention is given by simple considerations of symmetry.

The hydroquinones of the formula IV which are usable according to the invention can be di- or tetra-substituted. When two substituents are present, they always have to be identical and have to occupy the 2- and 5-positions. When four substituents are present, they have either to be identical or to be different in pairs, and in the latter case the one pair of substituents occupies the 2-position and the 5-position and the other pair the 3-position and the 6-position.

The resorcinols of the formula IV which are usable according to the invention can be mono-, di-, tri- or tetra-substituted. If one substituent is present, it can be in the 2- or 5-position. In the case of di-substituted resorcinols, the two substituents can be identical or different, with two identical substituents occupying either the 2-position and the 5-position or the 4-position and the 6-position, and two different substituents the 2-position and the 5-position. If three substituents are present, two have to be identical, with the two identical substituents in each case having to occupy the 4-position and the 6-position, whilst the third substituent can be in the 2-position or the 5-position. If there are four substituents, these have either to be identical or to be different in pairs, and in the latter case the one pair of substituents occupies the 2-position and the 5-position, and the other pair the 4-position and the 6-position. Furthermore, in the 4-position and the 6-position there can be two identical substituents, and in the 2-position and the 5-position two different substituents.

The brenzcatechins of the formula IV which are usable according to the invention can be di- or tetra-substituted. If two substituents are present, they have to be identical and can occupy the 3-position and the 6-position, or the 4-position and the 5-position. If four substituents are present, they have either to be identical or to be different in pairs, and in the latter case one pair of substituents occupies the 3-position and the 6-position and the other pair the 4-position and the 5-position.

It is possible with the process according to the invention to produce hydroxydiaryl ethers of the formula I which are practically free from diethers of the formula III. The process according to the invention is suitable in particular for producing those hydroxydiaryl ethers of the formula I wherein R, n and X have the meanings given under the formula I, whereby however, if two of the substituents $R_1$, $R_2$ and $R_3$ of the phenyl group of the formula II represent hydrogen, an alkyl group having 1 to 4 carbon atoms, an alkyl group which has 1 to 4 carbon atoms and which is mono- or disubstituted by halogen, phenyl, halogen, carboxyl or alkoxycarbonyl having 1 to 4 carbon atoms in the alkyl group, the third substituent has to be nitro, cyano or benzoyl; and, if one of the substituents $R_1$, $R_2$ and $R_3$ of the phenyl group of the formula II represents trifluoromethyl, at least one of the other two substituents has to be trifluoromethyl, nitro, cyano or benzoyl.

The process according to the invention is based on the observation that aromatic diethers of the formula III can, in the presence of alkali, be transetherified with dihydroxybenzenes of the formula IV to hydroxydiaryl ethers of the formula I. On the basis of this observation, the process according to the invention can be performed, as described above, by starting with diethers of the formula III and transetherifying these, in the presence of alkali, with dihydroxybenzenes of the formula IV. There is however also the possibility of utilising this transetherification reaction by a process in which the diethers of the formula III formed as by-products in the reaction of a halogenobenzene of the formula V with a monoalkali salt of a dihydroxybenzene of the formula IV are transetherified in situ without isolation. A preferred variant of the process according to the invention comprises therefore reacting a dhydroxybenzene of the formula IV in a polar aprotic solvent, in the presence of 1.2 to 2 equivalents of alkali per mole of dihydroxybenzene of the formula IV, with 0.9 to 1.0 mole of a halogenobenzene of the formula V. The diethers of the formula III intermediately occurring in the process as by-products are then transetherified, in the presence of the excess alkali, with the unreacted dihydroxybenzene of the formula IV to hydroxydiaryl ethers of the formula I, and hydroxydiaryl ethers of the formula I are obtained as a homogeneous reaction product. The aforementioned advantageous variant of the process according to the invention is especially suitable for producing those hydroxydiaryl ethers of the formula I wherein R, n and X have the meanings given under the formula I, whereby however, if two of the substituents $R_1$, $R_2$ and $R_3$ of the phenyl group of the formula II represent hydrogen, an alkyl group having 1 to 4 carbon atoms, an alkyl group which has 1 to 4 carbon atoms and which is mono- or disubstituted by halogen, phenyl, halogen, carboxyl or alkoxycarbonyl having 1 to 4 carbon atoms in the alkyl group, the third substituent has to be nitro, cyano or benzoyl, and, if one of the substituents $R_1$, $R_2$ and $R_3$ of the phenyl group of the formula II represents trifluoromethyl, at least one of the other two substituents has to be trifluoromethyl, nitro, cyano or benzoyl.

The process according to the invention is further illustrated by the Examples which follow.

ide, and the solution is stirred for one hour in a nitrogen atmosphere at 90° C. The cooled reaction solution is afterwards poured into 250 ml of ice water, and the pH value is adjusted to 3 to 4 by the addition of concentrated hydrochloric acid, whilst the reaction product precipitates in crystalline form. It is filtered off, and dried at 50° C. in a vacuum drying chamber. In this manner is obtained 26.5 g (95% of theory) of 2'-cyano-4'-trifluoromethyl-4-hydroxydiphenyl ether having a melting point of 130° to 133° C.

Further diethers of the formula III are reacted in an analogous manner to hydroxydiphenyl ethers of the formula I. The results of these tests are summarised in the following Table.

| Diethers of the formula III | m.p. (°C.) | Hydroxydiphenyl ethers of the formula I | Yield % of theory | m.p. (°C.) | b.p. °C./mm/Hg |
|---|---|---|---|---|---|
| 1,4-bis-(4'nitro-phenoxy)-benzene | 236–238 | 4-nitro-4-hydroxy-diphenyl ether | 79.7 | 171–173 | |
| 1,4-bis-(2',4'-di-nitrophenoxy)-benzene | 248–250 | 2',4'-dinitro-4-hydroxydiphenyl ether | 78.2 | 129–130 | |
| 1,4-bis-(2'-nitro-4'-methylphenoxy)-benzene | 147–148 | 2'-nitro-4'-trifluoromethyl-4-hydroxydiphenyl ether | 75.0 | oil | |
| 1,4-bis-(2'-cyano-4'-nitrophenoxy)-benzene | 300–302 | 2'-cyano-4'-nitro-4-hydroxydiphenyl ether | 74.2 | 160–163 | |
| 1,4-bis-(2',6'-di-nitro-4'-trifluoro-methylphenoxy)-benzene | 298–300 | 2',6'-dinitro-4'-trifluoromethyl-4-hydroxydiphenyl ether | 81.4 | 120–122 | |
| 1,4-bis-(2'-chloro-4'-trifluoromethyl-phenoxy)-benzene | 103–104 | 2'-chloro-4'-trifluoromethyl-4-hydroxydiphenyl ether | 50 | — | 160/0.1 |
| 1,4-bis-(4'-trifluoro-methylphenoxy)-benzene | 86–88 | 4'-trifluoromethyl-4-hydroxydiphenyl ether | 50 | — | 160/0.1 |
| 1,4-bis-(4'-cyano-phenoxy)-benzene | 207–208 | 4'-cyano-4-hydroxy-diphenyl ether | 79.6 | 138–140 | — |
| 1,4-bis-(2'-cyano-4-chlorophenoxy)-benzene | 216–218 | 2'-cyano-4'-chloro-4-hydroxydiphenyl ether | 87.7 | 115–117 | — |

EXAMPLE 1

2'-Cyano-4'-trifluoromethyl-4-hydroxydiphenyl ether 22.4 g (0.05 mole) of 1,4-bis-(2'-cyano-4'-trifluoromethylphenoxy)-benzene, 6.6 g (0.06 mole) of hydroquinone and 3.3 g (0.05 mole) of pulverised potassium hydroxide are dissolved in 100 ml of dimethylsulphox-

EXAMPLE 2

4'-Nitro-4-hydroxydiphenyl ether 12.1 g (0.11 mole) of hydroquinone and 10.5 g (0.16 mole) of pulverised potassium hydroxide are dissolved in 70 ml of dimethylsulphoxide, and the solution is heated in a nitrogen atmosphere to 120° C. and subsequently stirred for 30 minutes at this temperature. There is then added dropwise in the course of 30 minutes a solution of 15.75 g (0.1 mole) of chloronitrobenzene in 30 ml of dimethylsulphoxide. After completion of the addition, stirring at 120° C. is maintained for one hour. The cooled solution is then poured into 300 ml of ice-water, and neutralised with concentrated hydrochloric acid, whereupon the formed 4'-nitro-4-hydroxydiphenyl ether precipitates in the form of crystals. The product is separated by filtration, and is dried in vacuo in a vacuum drying chamber a 50° C. There is thus obtained 22.2 g (96% of theory) of 4'-nitro-4-hydroxydiphenyl ether, m.p. 164°–166° C.

EXAMPLE 3

2'-Cyano-4'-trifluoromethyl-4-hydroxydiphenyl ether 12.1 g (0.11 mole) of hydroquinone and 11.85 g (0.18 mole) of pulverised potassium hydroxide are dissolved in 70 ml of dimethylsulphoxide, and the solution is heated in a nitrogen atmosphere to 90° C. and subsequently stirred for 30 minutes at this temperature. There is then added dropwise in the course of 30 minutes a solution of 20.55 g (0.1 mole) of 2-cyano-4-trifluoromethylchlorobenzene in 30 ml of dimethylsulphoxide. After completion of the addition, stirring is maintained at 90° C. for one hour. The cooled solution is then poured into 300 ml of ice-water, and neutralised with concentrated sulphuric hydrochloric acid, whereupon 2'-cyano-4'-trifluoromethyl-4-hydroxydiphenyl ether precipitates in crystalline form. The product is separated by filtration and dried at 50° C. in vacuo. There is thus obtained 25.5 g (97% of theory) of 2'-cyano-4'-trifluoromethyl-4-hydroxydiphenyl ether, m.p. 130°–132° C.

The following hydroxydiphenyl ethers of the formula I are produced in an analogous manner.

| Diphenyl ethers of the formula I | Yield (% of theory) | m.p. (°C.) | b.p. (°C./mm Hg) |
| --- | --- | --- | --- |
| 2',4'-dinitro-4-hydroxydiphenyl ether | 80 | 121–123 | — |
| 2'-cyano-4-nitro-4-hydroxydiphenyl ether | 91 | 158–160 | — |
| 2'-nitro-4'-trifluoromethyl | 80 | — | oil |
| 4'-nitro-3-hydroxydiphenyl ether | 58.9 | 79–84 | 185–195/0.03 |
| 2'-cyano-4'-trifluoromethyl-3-hydroxydiphenyl ether | 82.8 | — | 165–170/0.1 |
| 2-nitro-4'-trifluoromethyl-3-hydroxydiphenyl ether | 73.5 | — | 165/0.03 |
| 4'-nitro-2-hydroxydiphenyl ether | 74.5 | 105–107 | — |
| 2'-cyano-4'-trifluoromethyl-2-hydroxydiphenyl ether | 75 | 120–122 | 142–151/0.1 |
| 2'-cyano-4'-trifluoromethyl-5-methyl-3-hydroxydiphenyl ether | 70 | — | 165–170/0.01 |
| 2'-chloro-4'-trifluoromethyl-4-hydroxydiphenyl ether | 68 | — | 143/0.1 |
| 2'-cyano-4'-trifluoromethyl-4-hydroxydiphenyl ether | 97 | 130–132 | — |
| 4'-nitro-4-hydroxydiphenyl ether | 96 | 164–166 | — |
| 4'-trifluoromethyl-4-hydroxydiphenyl ether | 52 | — | 125/0.1 |
| 2'-cyano-4'-chloro-4-hydroxydiphenyl ether | 95 | 120–123 | — |
| 4'-cyano-4-hydroxydiphenyl ether | 75 | 133–136 | — |
| 2'-chloro-4'-nitro-4-hydroxydiphenyl ether | 25 | 148–151 | — |
| 3'-methyl-4'-nitro-4-hydroxydiphenyl ether | 83 | 96–100 | — |
| 2'-cyano-4'-trifluoromethyl-5-methyl-3-hydroxydiphenyl ether | 67.6 | — | 165–170/0.01 |
| 2'-nitro-4'-carboxy-4-hydroxydiphenyl ether | 65 | 183–186 | — |
| 4'-benzoyl-4-hydroxydiphenyl ether | 69 | 75–78 | — |
| 2-(4'-hydroxyphenoxy)-5-nitro-pyridine | 71 | 174–175 | — |
| 2-(4'-hydroxyphenoxy)-pyridine | 60 | 142–144 | — |
| 2-(4'-hydroxyphenoxy)-3,5-dichloropyridine | 94 | 88–90 | — |
| 2-(3'-hydroxyphenoxy)-3,5-dichloropyridine | 90 | 121–123 | — |

What is claimed is:

1. Process for producing hydroxydiaryl ethers of the formula I

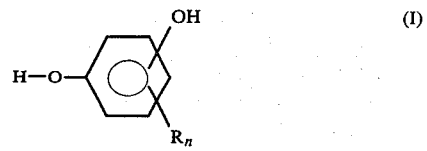

wherein R represents an alkyl group having 1 to 4 carbon atoms or chlorine, n represents 0, 1, 2, 3 or 4, and X represents a 2-pyridinyl group of the formula IIa or a 4-pyridinyl group of the formula IIb

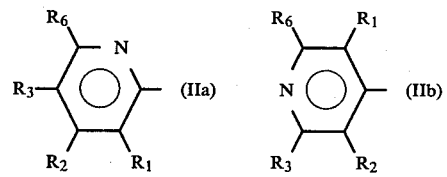

wherein $R_1$, $R_2$ and $R_3$ each represent hydrogen, an alkyl group having 1 to 4 carbon atoms, an alkyl group which has 1 to 4 carbon atoms and which is mono- or disubstituted by halogen, phenyl, halogen, carboxyl, alkoxycarbonyl having 1 to 4 carbon atoms in the alkyl group, trifluoromethyl, nitro, cyano or benzoyl, and $R_6$ has all the meanings given, with the exception of halogen, for $R_1$, $R_2$ and $R_3$, which process comprises reacting a diether of the formula III

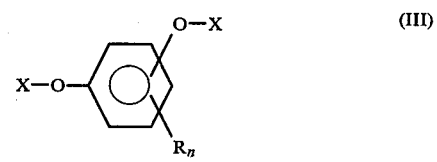

wherein R, n and X having the meanings given under the formula I, in a polar aprotic solvent, in the presence of 0.1 to 1 mole of alkali per mole of diether of the formula III, with a dihydroxybenzene of the formula IV

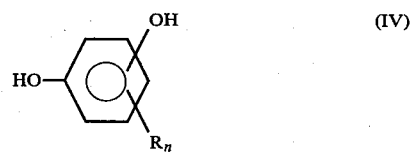

wherein R and n have the meanings given under the formula I.

2. Process according to claim 1, wherein a diether of the formula III is reacted, in the molar ratio of 1:1 to 1:1.1. with a dihydroxybenzene of the formula IV.

3. Process according to claim 1, wherein the reaction of a diether of the formula III with a dihydroxybenzene of the formula IV is performed at a temperature of between 40° and 200° C.

4. Process according to claim 1, wherein the reaction of a diether of the formula III with a dihydroxybenzene of the formula IV is performed at a temperature of between 80° and 150° C.

5. Process according to claim 1, wherein the polar aprotic solvent used is dimethylsulphoxide, dimethylformamide, dimethylacetamide, diethylacetamide, hexamethylphosphoric acid triamide, tetramethylurea, sulpholane, N-methylpyrrolidone, acetonitrile or methyl ether ketone.

6. Process according to claim 1, wherein there is used, besides the polar aprotic solvent, a further solvent which forms with water an azeotrope.

7. Process according to claim 1, wherein dimethylsulphoxide is used as the polar aprotic solvent.

8. Process according to claim 1, wherein there are used as alkaline substances, in the presence of which the reaction of a diether of the formula III with a dihydroxybenzene of the formula IV is performed, hydroxides, carbonates and hydrogen carbonates of alkali metals, preferably sodium hydroxide and potassium hydroxide.

9. Process according to claim 1, wherein the alkaline substance, in the presence of which the reaction of a diether of the formula III with a dihydroxybenzene of the formula IV is performed, is used in an amount of 0.1 to 1 equivalent per mole of dihydroxybenzene of the formula IV.

10. Process according to claim 1, wherein the alkaline substance, in the presence of which the reaction of a diether of the formula III with a dihydroxybenzene of the formula IV is performed, is used in an amount of 1 equivalent per mole of dihydroxybenzene of the formula IV.

11. Process according to claim 1, wherein the diethers of the formula III, formed as by-products in the reaction of a halogenobenzene of the formula V in a polar aprotic solvent with a monoalkali salt of a dihydroxybenzene of the formula IV, are reacted, without isolation, directly in the reaction mixture, in the presence of an additional amount of alkali substance, with the unreacted dihydroxybenzene of the formula IV to give hydroxydiaryl ethers of the formula I.

12. Process according to claim 11, wherein a dihydroxybenzene of the formula IV is reacted in a polar aprotic solvent, in the presence of 1.2 to 2 equivalents of alkaline substance per mole of dihydroxybenzene of the formula IV, with 0.1 to 1.0 mole of a halogenobenzene of the formula V.

* * * * *